United States Patent [19]

Yablonski

[11] Patent Number: 4,933,356
[45] Date of Patent: Jun. 12, 1990

[54] DIFLUNISAL POTENTIATION OF ACETAZOLAMIDE IN THE CONTROL OF INTRAOCULAR PRESSURE

[75] Inventor: Michael E. Yablonski, Cos Cob, Conn.

[73] Assignee: Cornell Research Foundation, Inc., Ithaca, N.Y.

[21] Appl. No.: 224,591

[22] Filed: Jul. 26, 1988

[51] Int. Cl.$^5$ .................. A61K 31/41; A61K 31/505; A61K 31/44
[52] U.S. Cl. .................................. 514/361; 514/274; 514/339; 514/363; 514/359; 514/384
[58] Field of Search ............... 514/361, 363, 256, 249, 514/241, 369

[56] References Cited

U.S. PATENT DOCUMENTS

| | | | |
|---|---|---|---|
| 2,554,816 | 5/1951 | Clapp et al. | 260/290 |
| 2,980,679 | 4/1961 | Pala | 260/256.5 |
| 3,714,226 | 1/1973 | Ruyle et al. | 260/473 S |
| 3,991,206 | 11/1976 | Tolman et al. | 424/317 |
| 4,305,927 | 12/1981 | Theeuwes et al. | 424/15 |
| 4,438,123 | 3/1984 | Smith | 424/270 |
| 4,483,864 | 11/1984 | Barfknecht et al. | 424/270 |
| 4,619,939 | 10/1986 | Maren | 514/363 |
| 4,636,515 | 1/1987 | Barfknecht et al. | 514/363 |

OTHER PUBLICATIONS

Verbeeck, R. K. et al., Clin. Pharmacokinet., 8:297 (1983).
Steelman, S. L. et al., Clin. Ther., 1(Suppl):1 (1978).
Tempero, K. F. et al., Br. J. Clin. Pharmacol., 4(Suppl):31S (1977).
Davies, R. O., Pharmacotherapy, 3:9S (1983).
Verbeeck, R. K. et al., Biochem. Pharmacol., 29:571 (1980).
Maren, T. H., J. Pharmacol. Exp. Ther., 130:26 (1980).
Serlin, M. J. et al., Clin. Pharmacol. Ther., 28:493 (1980).
Van Hacken, A. M. et al., Br. J. Clin. Pahrmacol., 20:225 (1985).
Maren, T. H. et al., Invest. Ophthalmol. Vis. Sci., 16:730 (1977).
Weiner, I. M. et al., Bull. Johns Hopkins Hosp., 105:286 (1959).
Sweeney, K. R. et al., Clin. Pharmacol. Ther., 40:518 (1986).
Maren, T. H., Physiol. Rev., 47:595 (1967).

Primary Examiner—Douglas W. Robinson
Assistant Examiner—Zohveh A. Fay
Attorney, Agent, or Firm—Jones, Tullar & Cooper

[57] ABSTRACT

The invention relates to an improved therapy to control intraocular pressure (IOP). More specifically, the present invention relates to an improved treatment of glaucoma patients to control ocular hypertension. It has now been found that an effective amount of diflunisal potentiates the action of certain heterocyclic sulfonamides such as acetazolamide to provide an improved hypotensive therapy.

18 Claims, 1 Drawing Sheet

DIFLUNISAL POTENTIATION OF ACETAZOLAMIDE IN THE CONTROL OF INTRAOCULAR PRESSURE

BACKGROUND OF THE INVENTION

Diflunisal, a fluorinated salicylate, exhibits analgesic, anti-inflammatory and antipyretic properties, and at high doses inhibits prostaglandin synthesis. It is well absorbed from the intestines and reaches peak plasma levels within 2–3 hours; steady state plasma levels are reached within 3–9 days on a regimen off 500 mg twice daily. Plasma Diflunisal is 99.83% protein bound and it is excreted mostly in the urine as a glucuronide. Diflunisal is generally better tolerated than aspirin and the most frequent adverse reactions are nausea, gastrointestinal discomfort and diarrhea.

The inhibitory action of diflunisal on cyclooxygenase metabolism has been represented by: Verbeeck, R. K. et al., Clin. Pharmac., 8:297 (1983); Steelman, S. L. et al., i Clin. Ther. 1(Suppl):1 (1978); Tempero, K. F. et al., Br. J. Clin. Pharmacol., 4(Suppl):31S (1977); and by Davis, R. O., Pharmacotherapy, 3:9S (1983). However, no ocular effects have been reported. Diflunisal has exceptionally high binding to plasma albumin, 99.83% at a concentration of 50 μm/ml, and thus can unbind partially bound compounds such as salicylic acid and phenprocoumin (Verbeeck, R. K., et al, Biochem. Pharmacal. 29:571 (1980)).

Examples of heterocyclic sulfonamides and phenylbenzoic acid compounds useful in the practice of this invention are given in U.S. Pat. Nos. 3,714,226 (Ruyle et al); 2,980,679 (Pala et al); 2,554,816; 4,636,515 and 4,483,864 (Barfknecht et al); 3,991,206 (Tolman et al); 4,305,927 (Theeuwes et al); 4,438,123 (Smith); and in 4,619,939 (Maren); all of which are included herein by reference. Topical application of sulfonamides for the reduction of intraocular pressure is shown in U.S. 4,619,939; U.S. 483,864; U.S. 4,438,123 and in U.S. 4,636,515. Sulfonamides and their preparation are shown in U.S. 2,980,679 and U.S. 554,816. The oral administration of acetazolamide for controlling intraocular pressure is shown in U.S. 4,305,927. In U.S. 3,714,226 various 5-(phenyl) benzoic acid compounds are shown to be useful anti-inflammatory compounds. Topical application of p-biphenylacetic acid as an ocular inflammatory agent is shown in U.S. 3,991,206.

SUMMARY OF THE INVENTION

Figure 1:
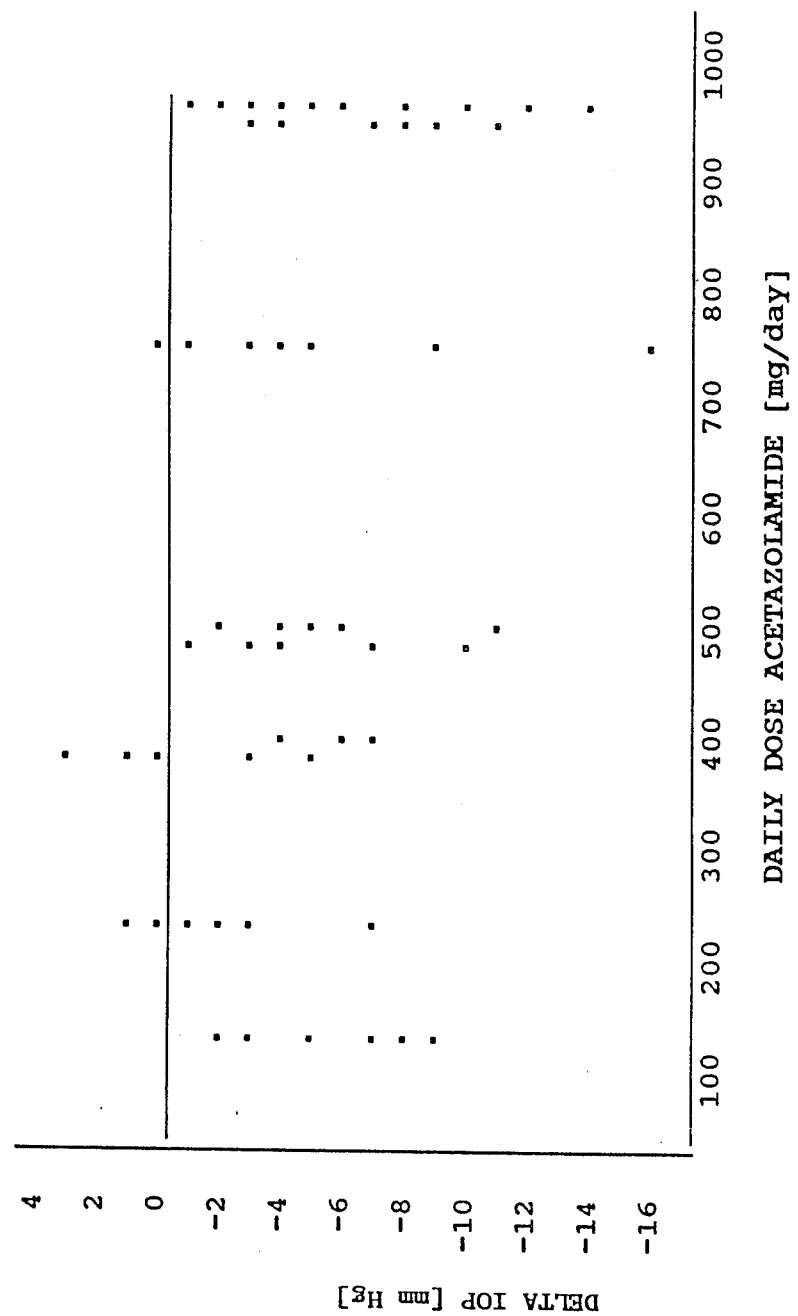
FIG. 1 is a plot of daily acetazolamide Dosage (mg/day) versus change in intraocular pressure in glaucoma patients after one week treatment with diflunisal (m=55 ayes).

An object of the present invention is a composition and method to reduce intraocular pressure in glaucoma subjects which comprises conjointly administering a heterocyclic sulfonamide, as for example acetazolamide, together with a substituted phenylbenzoic acid type compound, such as a diflunisal, in an amount effective to potentiate the heterocyclic sulfonamide.

Another object is a hypotensive medication comprising diflunisal taken in conjunction with a heterocyclic sulfonamide such as acetazolamide wherein the medication is administered to human and/or animal subjects orally or by other methods including topical administration absorption through the skin.

A further object is a method for increasing the level of free acetazolamide in human and animal plasma in the treatment of hypertension.

DETAILED DESCRIPTION OF THE INVENTION

The present invention relates to a composition and method for controlling intraocular pressure (IOP) in glaucoma patients, to the enhancement of the heterocyclic sulfonamide plasma levels and to a hypotensive therapy. More specifically the present invention relates to the action of flunisal compounds in potentiating the hypotensive effect of known acetazolamide compounds.

A composition useful in reducing intraocular pressure in subjects suffering from glaucoma comprises an heterocyclic sulfonamide compound and diflunisal compound; said diflunisal compound having a formula:

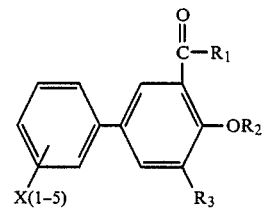

wherein X is fluro; $R_1$ is hydroxy or phenoxy; $R_2$ is hydrogen or lower alkanoyl; and $R_3$ is hydrogen; said heterocyclic sulfonamide having a formula:

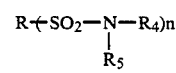

where R is a heterocyclic nitrogenous monovalent or divalent radical selected from the group consisting of benzothiazole-yl, 2-acetylamino-1,3,4-thiadiazole-yl, benzimidazol-yl, 1-phenylimidazole-yl, 5-acetylaminopyridine-yl, 4,6-dimethylpyrimidine-yl, pyrido-(2,1,C)-5-triazole-yl and 1,2-triazole-yl; $R_4$ and $R_5$ are independently selected from the group hydrogen, hydroxyl and $C_{1-6}$ alkyl and n=1 or 2.

Especially useful compositions of the above type comprise diflunisal compounds where X is 2; $R_1$ is hydroxy; R2 is hydrogen; and heterocyclic sulfonamide compounds where R is a monovalent benzothiazole-2-yl radical or a 2-acetylamino-1,3,4-thiadiazoleyl radical and $R_4$ and $R_5$ are hydrogen and/or methyl but preferably where both are hydrogen. The useful compositions include pharmaceutically acceptable salts and formulations of the above compounds. A preferred combination is where the acetazolamide is 5-acetamido-1,3,4-thiadiazole-2-sulfonamide and the diflunisal compound is 2-(hydroxy)-5-(2,4-difluorophenyl) benzoic acid.

Another aspect of the present invention relates to a method for treating subjects suffering from glaucoma which comprises administering conjointly to the subject an acetazolamide of the type set forth above together with an amount of a diflunisal compound (set forth above) effective to enhance the activity of the acetazolamide and to potentiate the hypotensive effect of the acetazolamide compound.

Also contemplated is a method for increasing the level of free acetazolamide compound in human and animal plasma which comprises administering conjointly to said human or animal an heterocyclic sulfonamide compound or a pharmaceutically acceptable non-toxic salt thereof and an amount of diflunisal compound or a pharmaceutically acceptable non-toxic salt thereof effective to increase plasma level of the sulfonamide; said diflunisal having a formula as set forth above; and said sulfonamide compound having a formula as set forth above. Especially advantageous for the purposes of this invention are the sulfonamides having a formula:

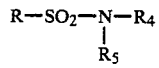

where R is a heterocyclic nitrogenous nonovalent radical selected from the group consisting of benzothiazole-2-yl, 2-acetlyamino-1,3,4-thiadiazole-5-yl, benzimidazole-2-yl, 1-phenylimidazole-2-yl, 5-acetylaminopyridine-2-yl, 4,6-dimethylpyrimidine-2-yl, pyrido-(2,1,C)-s-triazole-3-yl and 1,2,4-triazole-3-yl. A preferred combination is 5-acetamido-1,3,4-thiadiazole-2-sulfonamide used conjointly with 2-(hydroxy)-5-(2,4-difluorophenyl) benzoic acid.

Also contemplated is a method of enhancing the hypotensive activity and the blood plasma level of the described heterocyclic sulfonamide administered to a subject conjointly with an enhancing or potentiating amount of the diflunisal type compound sufficient to produce the hypotensive action, increase the blood plasma level of the sulfonamide and/or to lower the interocular pressure of the subject.

As used herein "conjointly" has its usual meaning and particularly at a time and in an amount such that the desired effect contributed by the compounds of the invention is in existence or comes into existence when the primary treatment effect is taking place.

Diflunisal, Chemical Abstracts Registry No. 22494-42-4, is commercially available under the trademark including Dolobid (Merck Sharpe & Dohme). One chemical name for diflunisal is 5-(2,4-difluorophenyl) salicylic acid. Useful derivatives for the purpose of this invention include the acid, pharmaceutical acceptable non-toxic salts of the acid and formulations thereof. The sodium salt is preferred for oral administration. When used herein diflunisal refers to related compounds, its salts and formulations.

Acetazolamide, Chemical Abstracts Registry No. 59-66-5 is commercially available under the trademark including Diamox (Lederle Laboratories) and generically. Another chemical name for acetazolamide is 2-acetylamino-1,3,4-thiadiazole-5 sulfonamide. Useful derivatives include pharmaceutical acceptable non-toxic salts and formulations thereof. The sodium salt is preferred particularly when administered in sustained release capsules. When used herein, acetazolamide refers generally to related compounds, their salts and/or formulations.

The mode of administration of the compounds of the invention can vary widely. The compounds, also formulated as pharmaceutically acceptable salts and in acceptable carriers, are preferably administered orally. Other methods of administration of either or both the diflunisal compound and the acetazolamide compound are ocular inserts, osmotic sustained release pumps and transdermal patches.

For purposes of the present invention, a useful daily dosage of an acetazolamide type compound is from about 125 mg to about 1000 mg.

A useful daily range of diflunisal type compounds to be administered conjointly with and for the purpose of potentiating acetazolamide type compounds is from about 500 mg to about 1000 mg. A preferred daily dosage comprises about 1000 mg diflunisal type compound with about 250 mg acetazolamide type compound.

The following examples are generally illustrative of the invention and should not be interpreted as limiting the invention.

EXAMPLE 1

All subjects taking part in this study participated voluntarily and an informed consent was obtained from each prior to their enrollment in the study. Forty-eight glaucoma patients (19 men and 29 women) on maximally tolerated antiglaucoma medications were assigned consecutively to the study. Their medical regimen included acetazolamide in 28 patients or methazolamide in 4 patients. All eyes were treated with at least one preparation of topical antiglaucoma medications; pilocarpine (60 eyes), epinephrine or dipivefrin hydrochloride (27 eyes), timolol, levobunolol or betaxolol (80 eyes), and echothiophate iodide (17 eyes). Upon entering the study each patient received a full ophthalmologic examination which included a visual acuity determination, slitlamp examination, IOP measurement (baseline) with a Goldmann applanation tonometer, gonioscopy, and a dilated fundus examination. Patients were instructed to take oral diflunisal, 500 mg, twice daily for one week, while their regular antiglaucoma medications remained unchanged. A week later patients were examined again for visual acuity, slit lamp examination, IOP measurement and a history of side effects. Baseline and follow-up IOP was measured by the same investigator using the same tonometer at approximately the same time of day.

Eight normal volunteers (52.3±16.4 years) on no medications participated in this study as a control group to study the ocular hypotensive effect of diflunisal itself and were given oral diflunisal, 500 mg, twice daily for one week. The examinations before and after diflunisal were similarly taken as glaucoma patients described above.

In 15 acetazolamide-treated patients 2-3 cc of venous blood was drawn before and again, at the same time of day, after one week on diflunisal for determination of total plasma concentration of acetazolamide. The blood sample underwent centrifugation at 5000 rpm for 5 minutes, and the plasma was separated and refrigerated until analysis. In addition, the plasma of seven of these 15 acetazolamide-treated patients was subjected to dialysis for determination of binding to albumin.

A blood sample was also taken from six acetazolamide-treated patients twice at a one week interval without diflunisal treatment.

An in vitro study was performed for the effect of graded doses of diflunisal on the plasma binding of acetazolamide. Both drugs were added to plasma of a single non-glaucomatous individual and duplicate dialyses were done.

Acetazolamide was analyzed by assay against carbonic anhydrase (Maren, T. H., *J. Pharmacol. Exp. Therap.*. 130:26 (1960)). Dialysis was carried out in a specially constructed cell consisting of two chambers of 1 ml capacity separated by Spectra/Por membrane, MW cutoff 6,000–8,000, Spectrum Med. Industries. One ml plasma, after analysis for total drug, was introduced to one compartment and 1 ml physiological saline to the other. The solutions were each mixed for 18 hours at 25* and then analyzed and calculated for free and total drug.

RESULTS

In the glaucomatous eyes, a step-wise multiple linear regression test (Draper, A. et al, *Applied Regression Analysis.*, New York, Wiley and Sons, Inc., p. 178 (1966)) was done with the various antiglaucoma medications as the independent variables, and the percent IOP reduction as the dependent variable, showing a statistically significant correlation only with acetazolamide, (a multiple R-square of 0.3285, $P<0.0001$, Table 1). The additional diflunisal treatment in acetazolamide-treated patients resulted in IOP levels which were significantly lower than baseline ($P<0.002$, paired t-test) with a mean reduction of $4.3\pm3.4$ mm Hg (Table 1)).

As shown in Table 1 the addition of diflunisal treatment in acetazolamide-treated patients resulted in IOP levels which were significantly lower than baseline with a mean reduction of $3.8\pm3.1$ (SD) mm Hg. Methazolamide-treated patients showed a small but significant decrease in IOP of $1.6\pm1.5$ mm Hg. Patients on topical medications alone and normal controls showed no significant change in IOP after diflunisal. FIG. 1 shows that there was no relationship between the daily dosage of acetazolamide and the IOP reduction.

Side effects were confined to the acetazolamide group and included mild gastrointestinal symptoms (8 patients), fatigue (7 patients), paresthesia (2 patients) and confusion (1 patient): all of which were well tolerated. Two additional patients on acetazolamide were dropped from the study because of severe nausea and extreme confusion which required them to discontinue diflunisal before the one week follow-up examination.

Total acetazolamide levels of plasma in 15 patients on diflunisal treatment were significantly higher than baseline levels ($31.8\pm16.1$ and $19.1\pm9.1$ uM, respectively, $P<0.015$, paired t-test). Plasma unbound acetazolamide concentrations in seven patients increased from $4.3\pm2.7\%$ to $16.2\pm8.7\%$ after diflunisal. These effects resulted in an increase of free acetazolamide from $1.0\pm0.6$ uM to $5.6\pm4.1$ uM. In a comparable group of six acetazolamide-treated patients without additional diflunisal, total acetazolamide plasma levels showed no significant change after a one week interval ($P\geq0.05$, paired t-test).

Table 2 shows the effect of graded doses of diflunisal on the plasma binding of acetazolamide in vitro. The two higher concentrations of diflunisal are equivalent to those following the dose using 500 mg twice daily. These in vitro results closely parallel those seen in vivo in glaucoma patients.

DISCUSSION

The above results demonstrate that the addition of diflunisal to glaucoma patients on acetazolamide yielded a significant decrease in IOP. When given alone or in addition to topical glaucoma medications or methazolamide, diflunisal treatment did not result in a significant reduction of IOP. In acetazolamide-treated patients the addition of diflunisal was associated with a nearly 50% increase in total plasma levels, and 5.6-fold increase in free plasma levels of acetazolamide.

This is the first report of the ocular hypotensive effect of the concomitant use of diflunisal and acetazolamide, and the interaction of the two compounds on plasma protein. Diflunisal has been shown to displace the following compounds from human plasma protein: salicylate and phenprocoumin (Verbeck, R. K. et al, *Biochem. Pharmacol.*, 29:571 (1980)), warfarin (Serlin, M. J. et al, *Clin. Pharmacol. Ther.*, 28:493 (1980)), and oxazepam (VanHacken, A. M., *Br. J. Clin. Pharmacol.*, 20:225 (1985)). Interestingly, the magnitude of the change induced by acetazolamide appears greater than any of these four compounds.

The present invention shows that diflunisal competes with acetazolamide for binding sites on plasma albumin. Since the former drug is 99.83% (Verbeck, R. K., supra) bound and the latter 93–97% bound, it is not surprising that the effect of diflunisal is strong enough to reduce acetazolamide binding to around 80%. The unbound plasma concentration of acetazolamide increased from 1.0 to 5.6 uM, which apparently caused an additional decrease in IOP. It is significant that this range of unbound concentration is at a steep part of the dose-response curve in rabbits (Maren, T. H., et al, *Invest. Opthalmol. Vis. Sci.*, 16:730 (1977)).

Salicylate has been shown to unbind acetazolamide from plasma proteins (Sweeney, K. R., et al, *Clin. Pharmacol. Ther.*, 40:518 (1986)): A second effect of the combinations of diflunisal and acetazolamide is to raise total plasma concentrations of acetazolamide: this is in accord with the acidic nature of both compounds in that they are both secreted by the kidney (Davies, R. O., *Pharma. Therapy*, 3:9S (1983); Weiner, I. M., *Bull. Johns Hopkins Hosp.*, 105:286 (1959)). Without wishing to be bound to a particular theory it is suggested that diflunisal, like salicylate, potentiates acetazolamide's ocular hypotensive effect as a result of displacement of protein bound acetazolamide and the reduction in acetazolamide renal clearance, by competitive inhibition.

Diflunisal did not affect the hypotensive action of methazolamide in the few patients studied. This inhibitor is only 55% bound to plasma protein, and unbinding, if it occurs, could not be of great magnitude.

Two patients out of 30 patient on acetazolamide developed side effects severe enough to cause them to be excluded from the study after the addition of diflunisal. In the remaining patients 18 showed mild but tolerable side effects of gastrointestinal disturbance, paresthesia, fatigue and dizziness.

The combination acetazolamide-diflunisal treatment gives an IOP lowering effect, which is unattainable with the current antiglaucoma medication. It is expected that smaller doses of acetazolamide will cause fewer side effects.

The above compositions and formulations thereof including commercial formulations sold under various trademarks are for this purpose preferably administered orally. Other means of administering these components include topical applications and absorption through the skin using absorption enhancement means.

EXAMPLE 2

When the procedure of Example 1 is repeated using in place of the acetazolamide heterocyclic sulfonamides of the formula $R-SO_2-N-H_2$ where the R-substituent is benzothiazole-2-yl, benzimidazole-2-yl, 1-phenylimidazole-2-yl, 5-acetylamilopyridine-2-yl, 4,6- dimethylpyrimidine-2-yl, pyrido-(2,1,C)-s-triazole-3-yl or 1,2,4-triazole-3-1, similar hypotensive effects, enhanced plasma levels and synergistic intraocular pressure reductions in glaucoma patients will be obtained.

TABLE I

CHANGES IN INTRAOCULAR PRESSURE FOLLOWING DIFLUNISAL TREATMENT

| Group | Baseline IOP (mm Hg) | Change in IOP (mm Hg)[a] | p value of |
|---|---|---|---|
| *Acetazolamide n = 55 eyes | 18.3 ± 6.1 | −3.8 ± 3.1 | <0.0001 |
| **Methazolamide N = 10 eyes | 17.6 ± 2.1 | −1.6 ± 1.5 | <0.02 |
| *Topically Treated Only n = 22 eyes | 18.8 ± 4.0 | −0.7 ± 2.1 | N.S. |
| ***Control n = 16 eyes | 15.6 ± 3.7 | 0.0 ± 1.0 | N.S. |

*Acetazolamide - when antiglaucoma treatment included acetazolamide in various doses in addition to various topically applied antiglaucoma medications.
**Methazolamide - when antiglaucoma treatment included methazolamide in various doses in addition to various topically applied medications.
[a]Probability for difference between before and after diflunisal treatment, based on paired t-test.
[b]Values are means ± SD.

TABLE II

PLASMA BINDING OF ACETAZOLAMIDE[a]

| Diflunisal μm | % unbound acetazolamide |
|---|---|
| 0 | 7 |
| 200 | 14 |
| 400 | 22 |
| 600 | 26 |

[a]In Vitro plasma binding of 90 μM acetazolamide in a single individual (T.H.M.) following graded concentrations of diflunisal.

What is claimed is:

1. A composition useful in reducing intraocular pressure in subjects suffering from glaucoma which comprises a therapeutically effective amount of a heterocyclic sulfonamide compound and a diflunisal compound; said diflunisal compound having a formula:

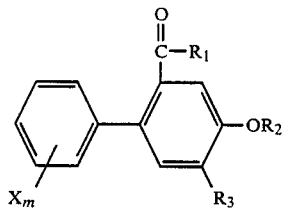

wherein X is fluoro; m=1 to 5; $R_1$ is hydroxy or phenoxy; $R_2$ is hydrogen or lower alkanoyl; and $R_3$ is hydrogen; said heterocyclic sulfonamide having a formula:

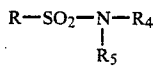

where R is a heterocyclic nitrogenous radical selected from the group consisting of benzothiazole-2-yl, 2-acetylamino-1,3,4-thiadiazole-5-yl, benzimidazole-2-yl, 1-phenylimidazole-2-yl, 5-acetylamino-pyridine-2-yl, 4,6-dimethylpyrimimine-2-yl, pyriro(2,1,C)-S-Triazole-3-yl, 4,6-dimethylpyrimidine-2-yl, pyrido(2,1,C)-s-triazole-3-yl and 1,2,4-Triazole-3-yl; $R^4$ and $R^5$ are independently selected from the group hydrogen, hydroxyl and $C_{1-6}$ alkyl; and wherein the weight amount of heterocyclic sulfonamide is from about 125 to 1000 parts per 500 to 1000 parts diflunisal compound.

2. The composition of claim 1 wherein the $R_4$ and $R_5$ radicals of the heterocyclic sulfonamide are hydrogen.

3. The composition of claim 1 wherein the heterooyclic sulfonamide is 2-acetylamino-1,3,4-thiadiazole-5sulfonamide.

4. The composition of claim 1 wherein the diflunisal compound is 2-(hydroxy)-5-(2,4-difluorophenyl) benzoic acid.

5. The composition of claim 3 wherein the diflunisal compound is 2-(hydroxy)-5-(2,4-difluorophenyl) benzoic acid.

6. The composition of claim 1 wherein the sulfonamide is 5-acetamido-1,3,4-thiadiazole-2-sulfonamide and the diflunisal compound is 2-(hydroxy)-5-(2,4-difluorophenyl) benzoic acid.

7. A method for increasing the level of heterocyclic sulfonamide compound in human and animal plasma which comprises administering conjoining to said human or animal a therapeutically effective amount of a heterocyclic sulfonamide compound or a therapeutically acceptable non-toxic salt thereof and a therapeutically effective amount of a diflunisal compound or a pharmaceutically acceptable non-toxic salt thereof to potentiate the plasma level of the said heterocyclic sulfonamide; said diflunisal having a formula:

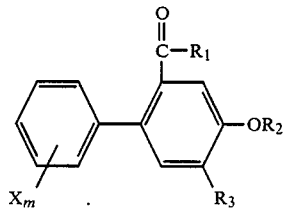

wherein X is fluoro and m=1–5; $R_1$ is hydroxy or phenoxy; $R_2$ is hydrogen or lower alkanoyl; and $R_3$ is hydrogen; said heterocyclic sulfonamide having a formula:

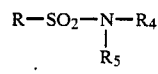

where R is a heterocyclic nitrogenous radical selected from the group consisting of benzothiazole-2-yl, 2-acetylamino-1,3,4-thiadiazole-5-yl, benzimidazole-2-yl, 1-phenylimidazole-2-yl, 5-acetylamino-pyridine-2-yl, 4,6-dimethylpyrimidine-2-yl, pyrido(2,1,C)-s-triazole-3-yl and 1,2,4-Triazole 3-4; $R^4$ and $R^5$ are independently selected from the group hydrogen, hydroxyl and $C_{1-6}$ alkyl; and wherein the weight amount of heterocyclic sulfonamide is from about 125 to 1000 parts per 500 to 1000 parts diflunisal compound.

8. The method of claim 7 wherein $R_4$ and $R_5$ radicals of the heterocyclic sulfonamide are either all hydrogen or hydrogen and $C_{1-6}$-alkyl.

9. The method of claim 7 wherein the R radical of the heterocyclic sulfonamide is 2-acetylamino-1,3,4-thiadiazole5-yl.

10. The method of claim 8 wherein the heterocyclic sulfonamide is 2-acetylamino-1,3,4-thiadiazole-5-sulfonamide.

11. The method of claim 7 wherein the diflunisal compound is 2-(hydroxy)-5-(2,4-difluorophenyl) benzoic acid.

12. The method of claim of claim 10 wherein the diflunisal compound is 2-(hydroxy)-5-(2,4-difluorophenyl) benzoic acid.

13. The method of claim 14 wherein the daily dosage of said sulfonamide is from about 125 mg to 1000 mg and the daily dosage of diflunisal is from about 500 mg to about 1000 mg.

14. A method for treating subjects suffering from glaucoma which comprises conjointly administering the heterocyclic sulfonamide and the diflunisal compound of claim 1; wherein the said diflunisal compound is administered in an amount sufficient to potentiate the hypotensive effect of the sulfonamide compound.

15. The method of claim 14 wherein the diflunisal compound and the sulfonamide compound are administered orally.

16. The method of claim 15 wherein one or more of the diflunisal and the sulfonamide compounds is administered by absorption through the skin.

17. A method of enhancing the hypotensive effect on a subject suffering from glaucoma of a heterocyclic sulfonamide which comprises administering conjointly to said subject with said sulfonamide, a potentiating amount of the diflunisal compound of claim 1.

18. The method of claim 17 wherein the diflunisal compound is 2-(hydroxy)-5-(2,4-difluorophenyl) benzoic acid and the acetazolamide is 5-acetamido-1,2,3-thiadiazole-2-sulfonamide.

* * * * *

UNITED STATES PATENT AND TRADEMARK OFFICE
CERTIFICATE OF CORRECTION

PATENT NO. : 4,933,356

DATED : June 12, 1990

INVENTOR(S) : Yablonski

It is certified that error appears in the above-identified patent and that said Letters Patent is hereby corrected as shown below:

Claim 1, column 7, line 64, bridging line 65, delete "4,6-dimethylpyrimimine-2-yl, pyriro (2,1,C)-S-Triazole-3-yl,".

Claim 3, column 8, line 5, change "heterooy" to --heterocy--;

Claim 3, column 8, line 6, bridging line 7, change "2-acetylamino-1,3,4-thiadiazole-5sulfunamide" to --2-acetylamino-1,3,4-thiadiazole-5-sulfonamide--.

UNITED STATES PATENT AND TRADEMARK OFFICE
CERTIFICATE OF CORRECTION

PATENT NO. : 4,933,356

DATED : June 12, 1990

INVENTOR(S) : Yablonski

It is certified that error appears in the above-identified patent and that said Letters Patent is hereby corrected as shown below:

Claim 7, column 8, line 21, change "conjoining" to --conjointly--;

Claim 7, column 8, line 54, change "1,2,4- Triazole 3-4" to --1,2,3-triazole-3-yl--.

Claim 18, column 10, line 14, bridging line 15, change "5-acetamido-1,2,3-thiadiazole-2-sulfonamide" to --5-acetamido-1,3,4-thiadiazole-2-sulfonamide--.

Signed and Sealed this

Thirteenth Day of October, 1992

Attest:

DOUGLAS B. COMER

Attesting Officer     Acting Commissioner of Patents and Trademarks

UNITED STATES PATENT AND TRADEMARK OFFICE
CERTIFICATE OF CORRECTION

PATENT NO. : 4,933,356
DATED : June 12, 1990
INVENTOR(S) : Yablonski

It is certified that error appears in the above-indentified patent and that said Letters Patent is hereby corrected as shown below:

Column 7, claim 1, line 64, bridging line 65, delete "4,6-dimethylpyrimimine-2-yl, pyriro (2,1,C)-S-Triazole-3-yl,".

Column 8, claim 3, line 5, change "heterooy" to --heterocy--

Column 8, claim 3, line 6, bridging line 7, change "2-acetylamino-1,3,4-thiadiazole-5sulfunamide" to --2-acetylamino-1,3,4-thiadiazole-5-sulfonamide--

UNITED STATES PATENT AND TRADEMARK OFFICE
CERTIFICATE OF CORRECTION

PATENT NO. : 4,933,356
DATED : June 12, 1990
INVENTOR(S) : Yablonski

It is certified that error appears in the above-indentified patent and that said Letters Patent is hereby corrected as shown below:

Column 8, claim 7, line 21, change "conjoining" to --conjointly--

Column 8, claim 7, line 54, change "1,2,4- Triazole 3-4" to --1,2,3-triazole-3-yl--

Column 10, claim 18, line 14, bridging line 15, change "5-acetamido-1,2,3-thiadiazole-2-sulfonamide" to --5-acetamido-1,3,4-thiadiazole-2-sulfonamide--

This Certificate supersedes Certificate of Correction issued Oct. 13, 1992.

Signed and Sealed this

First Day of March, 1994

Attest:

BRUCE LEHMAN

Attesting Officer

Commissioner of Patents and Trademarks